US007155396B2

(12) United States Patent
Yuyama et al.

(10) Patent No.: US 7,155,396 B2
(45) Date of Patent: *Dec. 26, 2006

(54) DRUG PREPARATION INSTRUCTION SYSTEM (75) Inventors: Hiroyuki Yuyama, Osaka (JP); Yoshito Goto, Osaka (JP)

(73) Assignee: Kabushiki Kaisha Yuyama Seisakusho, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 772 days.

(21) Appl. No.: 09/335,189

(22) Filed: Jun. 17, 1999

(65) Prior Publication Data
US 2002/0062227 A1    May 23, 2002

(30) Foreign Application Priority Data
Jun. 18, 1998    (JP)    ............................... 10-171440

(51) Int. Cl.
*G06Q 10/00*    (2006.01)
(52) U.S. Cl. .............................. 705/2; 705/3; 600/300
(58) Field of Classification Search ................ 705/2–3; 379/88.16; 709/238; 395/828
See application file for complete search history.

(56) References Cited

U.S. PATENT DOCUMENTS

| 4,733,362 | A | | 3/1988 | Haraguchi | .................. 364/479 |
| 4,847,764 | A | * | 7/1989 | Halvorson | ..................... 700/2 |
| 5,299,121 | A | * | 3/1994 | Brill et al. | .................. 622/301 |
| 5,537,626 | A | * | 7/1996 | Kraslavsky et al. | ........ 395/828 |
| 5,597,995 | A | * | 1/1997 | Williams et al. | ............ 235/375 |
| 5,604,692 | A | | 2/1997 | Yuyama | ...................... 364/788 |
| 5,648,751 | A | | 7/1997 | Yuyama et al. | ........ 340/309.15 |
| 5,713,485 | A | | 2/1998 | Liff et al. | ...................... 221/2 |
| 5,737,396 | A | * | 4/1998 | Garcia | .................... 379/88.16 |
| 5,758,095 | A | * | 5/1998 | Albaum et al. | ................ 705/2 |

FOREIGN PATENT DOCUMENTS

| EP | 724 210 | 7/1996 |
| JP | 8-131519 | 5/1996 |
| JP | 9-51922 | 2/1997 |

(Continued)

OTHER PUBLICATIONS

Tom Venetis, May 30, 1996, Computer Dealer News, Network management. (Markvision printer support software) (Software) (Evaluation), v12, n11, p. 51(2).*

(Continued)

*Primary Examiner*—Joseph Thomas
*Assistant Examiner*—Robert Morgan
(74) *Attorney, Agent, or Firm*—Wenderoth, Lind & Ponack, L.L.P.

(57) ABSTRACT

When drugs are prepared according to drug preparation order sheets printed by drug preparation order printers, it is desired to freely set the relation with the printers by setting data without directly connected and fixed to a control program of a control unit of a drug preparation order system so as to cope with e.g. relocations of drug preparation tables. As the drug preparation instruction system, a control unit and a plurality of drug preparation order printers are provided. In the data storage portion of the control unit, data showing the relation between drugs and drug types are stored. By reading drug type codes from inputted drug data, and by reading printer numbers corresponding to the respective drug type codes from a printer setting portion in which are stored data showing the relation between drug type codes and printer numbers, drug data are printed individually by the printers of the set numbers.

6 Claims, 8 Drawing Sheets

FOREIGN PATENT DOCUMENTS

WO 95/25423 9/1995
WO WO 9529455 A1 * 11/1995

OTHER PUBLICATIONS

Racher Press Inc. Feb. 15, 1999, New Generation of Printers Facilitates RX Operations, vol. 21, n4, p. RX 17.*

Tom Venetis, May 30, 1996, Compute Dealer News, Network management. (Markvision printer suport software) (Software) (Evaluation), v12, n11, p. 51(2).*

* cited by examiner

| drug code | drug name | unit | drug type code |
|---|---|---|---|
| kaite | external application drug D | sheets | 41 (external drug) |
| sani | powder drug E | mg | 21 (powder/packaged) |
| sanshi | powder drug C | g | 22 (powder/heat-sealed) |
| shoue | tablets A | piece | 11 (tablets/packaged) |
| shouhi | tablets B | piece | 12 (tablets/heat-sealed) |
| suiefu | liquid drug F | ml | 31 (liquid drug) |
| ⋮ | ⋮ | ⋮ | ⋮ |

FIG. 4

<setting the drug preparation instruction printers>

| drug type code | drug preparation instruction printer No. |
|---|---|
| 11 (tablets/packaged) | 0 |
| 12 (tablets/heat-sealed) | 1 |
| 21 (powder/packaged) | 0 |
| 22 (powder/heat-sealed) | 2 |
| 31 (liquid drug) | 0 |
| 41 (external drug) | 2 |
| ⋮ | ⋮ |

OK  cancel  renew

| \<input of drug preparation data\> | | | |
|---|---|---|---|
| patient No. 93026671<br>patient name Taro Yamada<br>sex 1 male<br>birth date May 6, 1945<br>age 52 years and 02 months | | voucher No. 1234<br>department : internal<br>MD : 0102 Kawakami Hanako<br>taking guidance: 1 Yes | |

| prescription No. | code  drug name /taking directions | dose | drug type | tray division |
|---|---|---|---|---|
| 1 | shoue  tablets A<br>/301  3 times a day<br>         after meals<br>      30 days | 6 pieces | 11 tablets<br>  /packaged | A |
| 2 | shouhi  tablets B<br>/301  3 times a day<br>         after meals<br>      30 days | 9 pieces | 12 tablets<br>  /heat-sealed | A |
| 3 | sanshi  powder drug C<br>/105  once a day<br>         before bedtime<br>      30 days | 2 g | 22 powder<br>  /heat-sealed | B |
| 4 | kaite  external drug D<br>/109  once a day<br>      30 days | 1 sheet | 41 external drug | B |

(number of prescriptions : 4)                    (number of trays : 2)

[ new entry ]   [ inspection OK ]   [ cancel ]

FIG. 8

```
[first printer]   *** drug preparation order sheet ***
patient No.    93026671            voucher No.       1234
patient name   Taro Yamada         department      : internal
sex            male                MD              : Kawakami Hanako
birth date     May 6, 1945         taking guidance: Yes
age            052 years and 02 months
```

| prescription No. | drug name /taking directions | dose | drug type | tray division |
|---|---|---|---|---|
| 2/4 | tablets B<br>3 times a day<br>  after meals<br>30 days | 9 pieces | tablets<br>/heat-sealed | A/2 |

FIG. 9

```
[second printer]   *** drug preparation order sheet ***
patient No.    93026671            voucher No.       1234
patient name   Taro Yamada         department      : internal
sex            male                MD              : Kawakami Hanako
birth date     May 6, 1945         taking guidance: Yes
age            052 years and 02 months
```

| prescription No. | drug name /taking directions | dose | drug type | tray division |
|---|---|---|---|---|
| 3/4 | powder drug C<br>once a day<br>  before bedtime<br>30 days | 2 g | powder<br>/heat-sealed | B/2 |
| 4/4 | external drug D<br>once a day<br>30 days | 1 sheet | external | B/2 |

A: tablet/packaged
B: tablet/heat-sealed
C: powder/packaged
D: powder/heat-sealed
E: liquid drug
F: external

DRUG PREPARATION INSTRUCTION SYSTEM

BACKGROUND OF THE INVENTION

This invention relates to a drug preparation instruction system having printers for printing prescription-based drug preparation instructions.

A typical such system uses a small computer such as a personal computer. Necessary data is entered and stored into the small computer from a host computer or through input means such as a keyboard. The necessary data may include patient names or numbers, drug types such as powders and tablets, drug names, dosage, and directions for administering the drugs.

Such a system also includes a plurality of printers each capable of printing drug preparation instructions for only one or one group of many different drug types.

The "drug types" include "tablets to be packaged", "heat-sealed tablets", "powder drugs to be packaged", "heat-sealed powder drugs", "liquid drugs" and "externally applied drugs". The term "to be packaged" means that the tablets or powder drugs are to be packaged by a packaging machine. The term "heat-sealed" means that tablets or powder drugs that have already been packaged and sealed are to be simply counted and delivered to patients as they are. But drugs may be categorized in different ways.

The reason why each printer is adapted to print drug print instructions for only one drug type or only one group of drug types is because different types of drugs are usually prepared at different drug preparation stations spaced from one another. Thus, by arranging a plurality of printers at each drug preparation station, pharmacists do not have to leave their position to check the printers. Printers are placed e.g. on drug preparation tables having drug storage shelves at the respective drug preparation stations.

Drugs prepared at the respective drug preparation stations are put in trays corresponding to respective patients. Trays have display means as disclosed in unexamined Japanese patent publication 8-131519, that display patient ID numbers and drug types, such as tablets and powder drugs. The trays may then be delivered to a drug delivery counter on a conveyor, as disclosed in unexamined Japanese patent publication 9-51922, or simply hand-carried to the counter.

Among the printers of this system, the printer for printing instructions for "heat-sealed tablets" is placed on a table at the heat-sealed tablet preparation station, and directly connected to the control circuit, which is programmed such that the printer prints only instructions about these types of drugs.

For example, the printer placed at the heat-sealed powder drug preparation station can print only instructions concerning heat-sealed powder drugs. Thus, a problem will arise if, due to relocations of drug preparation stations, it becomes necessary to use the printer at the powder drug preparation station as a printer for printing instructions for e.g. "heat-sealed tablets". In such a case, it is necessary to reprogram the control circuit altogether. Such reprogramming is extremely time-consuming and troublesome.

The same problem arises if it is necessary to add a new drug preparation station and thus a new printer for printing instructions concerning drugs prepared in this station. In such a case, too, the control circuit has to be reprogrammed altogether.

Another problem with this system is that information provided by each printer is far from enough. For example, the system does not provide information on whether patients should be given instructions for taking the drugs. The system additionally does not display information on whether drugs for a certain patient should be divided into a plurality of batches and put into a plurality of trays. In this system, information on whether instructions should be given to patients, that is, the doctor's orders on whether it is necessary to explain to patients how to take the drugs, which is written in doctor's order sheets, is prepared besides prescriptions and put into trays. Thus, a pharmacist at the drug delivery counter has to pick up and read the order sheet in every tray to determine whether or not he or she has to explain to the respective patient, how to take the respective drug.

Trays are usually stacked one on another for transportation. Thus, in order to pick up and read an order sheet in one tray, it is necessary to remove all the above trays. Order sheets in some or most trays may indicate that the customer needs instructions for taking the drugs. In any event, the pharmacist has to read all the order sheets in order to confirm that such guidance is not necessary. Delivering drugs to patients is thus time-consuming and tends to hinder smooth flow of the entire drug preparation line.

Conventional drug preparation instruction sheets contain no information on dividing drugs for one patient into a plurality of batches to put each batch in a separate tray, because no one has ever thought of such a thing. Thus, if a large amount of drugs are prescribed for one patient, the drugs tend to partially fall off while being transported on a single tray. Thus, it is often necessary to send drug preparation instruction sheets in a tray separately from prescribed drugs.

An object of this invention is to provide a drug preparation instruction system which is free of these problems.

SUMMARY OF THE INVENTION

According to this invention, there is provided a drug preparation order system comprising a control unit for carrying out logic operations and outputting control signals based on externally inputted drug preparation data including a patient name or a patient code, drug codes, taking directions and dosage, and a plurality of printers connected to the control unit for printing on drug preparation order sheets in response to the control signals, the control unit having a data storage portion for storing basic data about drug codes including drug type codes, patient name and taking directions, and a printer setting portion for setting the correlation between the drug type codes and the printer, whereby reading drug type codes of drugs necessary for a patient from among the drug preparation data inputted in the data storage portion, setting data of the printer corresponding to the drug type codes by the printer setting portion, and printing on a drug preparation order sheet data including the patient name and the prescribed drug names by the printer in the set data.

In the above system, when drug preparation data is inputted into the control unit, by reading drug type codes from the data storage portion and by reading printer numbers corresponding to the respective drug type codes from the printer setting portion, drug data for respective patients is printed individually on drug preparation instruction paper by a plurality of printers.

On the printer setting portion, data showing the correlation between the drug type codes and the printer numbers are recorded. By reading the printer number from the printer setting portion, it is automatically set by which printer the drug preparation instruction should be printed. If the layout of a pharmacy is changed, setting can be easily changed by re-setting the correlation.

Other features and objects of the present invention will become apparent from the following description made with reference to the accompanying drawings, in which:

DETAILED DESCRIPTION OF THE PREFERRED EMBODIMENT

Figure 1:
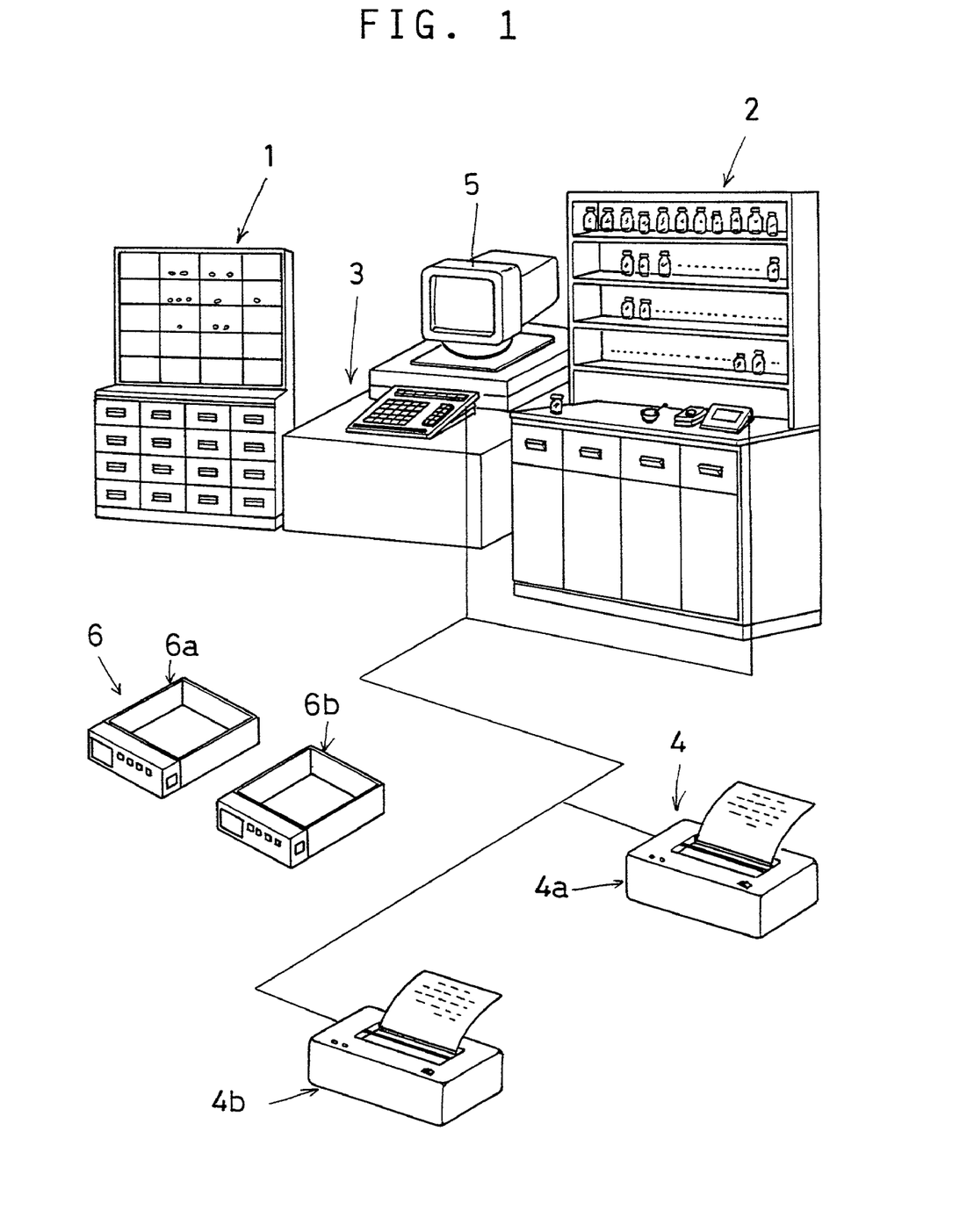
FIG. 1 is a schematic view of a drug preparation instruction system embodying the invention.

An embodiment of this invention is now described with reference to the drawings. As shown in FIG. 1, the drug preparation instruction system embodying the present invention comprises a control unit 3 provided e.g. between a drug preparation table 1 having a shelf in which are stored various kinds of tablets and a drug preparation table 2 having a shelf for keeping powdered drugs, and a plurality of (two in the embodiment) printers 4 (4a, 4b). Numeral 5 indicates a CRT display. Numerals 6 (6a, 6b) are trays.

Figure 2:
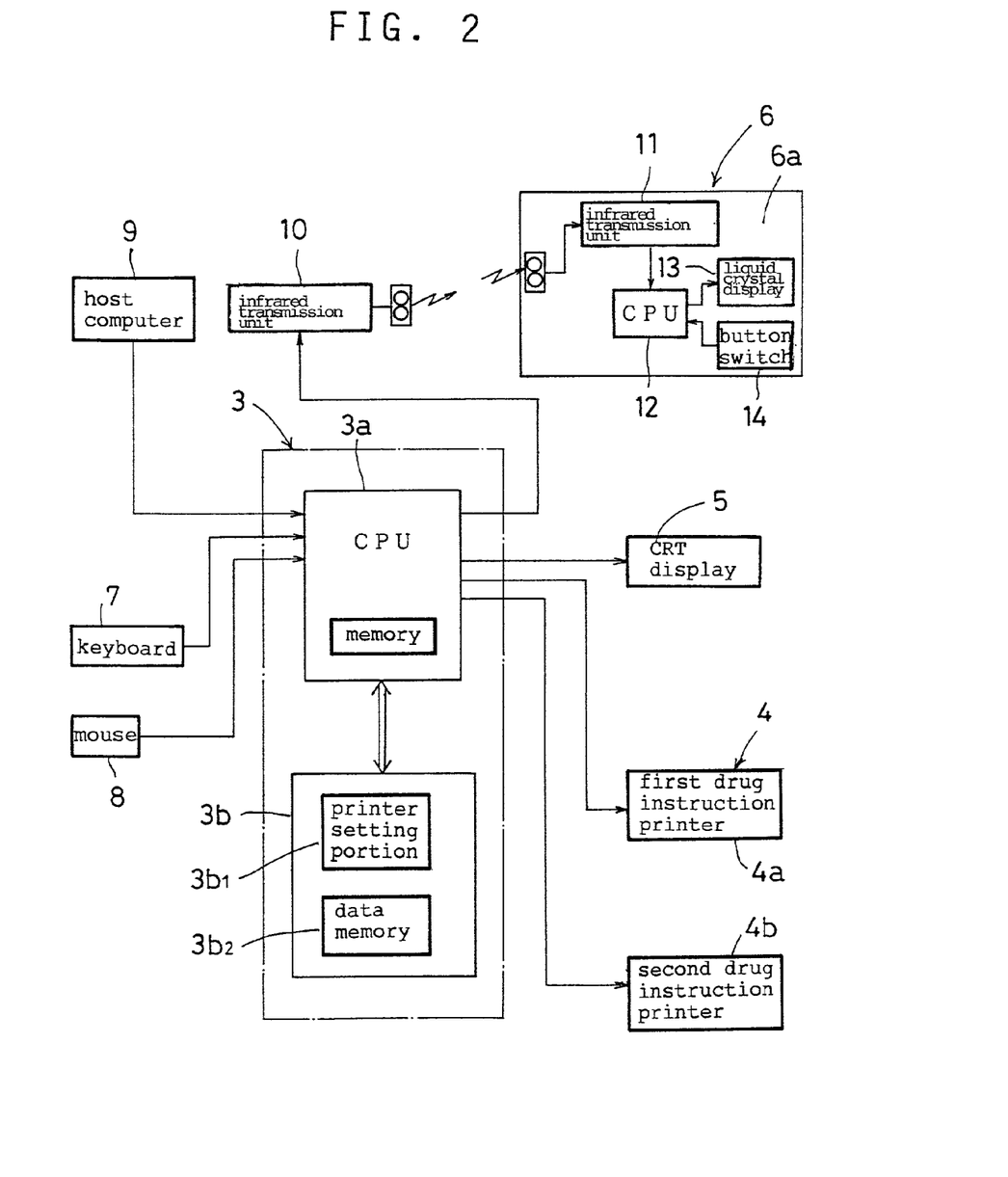
FIG. 2 is a control block diagram of the system.

FIG. 2 is a block diagram schematically showing the entire drug preparation system. As shown, the control unit 3 is a small personal computer (PC for short) including a CPU (central processing unit) 3a and an external memory 3b, called a file device. The CPU 3a has a memory for storing input data. The external memory 3b comprises a printer setting memory 3b1 and a data memory 3b2, which will be described later.

As input means, a keyboard 7 and a mouse 8 are connected to the CPU 3a. A host computer 9, is also connected to the CPU, to enter prescription data through communication lines. But the host computer 9 is not an essential element. Numeral 10 indicates an infrared transmission unit through which necessary parts of the prescription data are radio-transmitted to the trays 6. Instead of infrared transmission, a contact transmission or any other wireless transmission may be used. One or a plurality of (e.g. two or three) trays 6a and 6b are used to transport drugs for one patient. The CPU transmits necessary parts of the prescription data to each tray for the one patient.

Figure 10A:
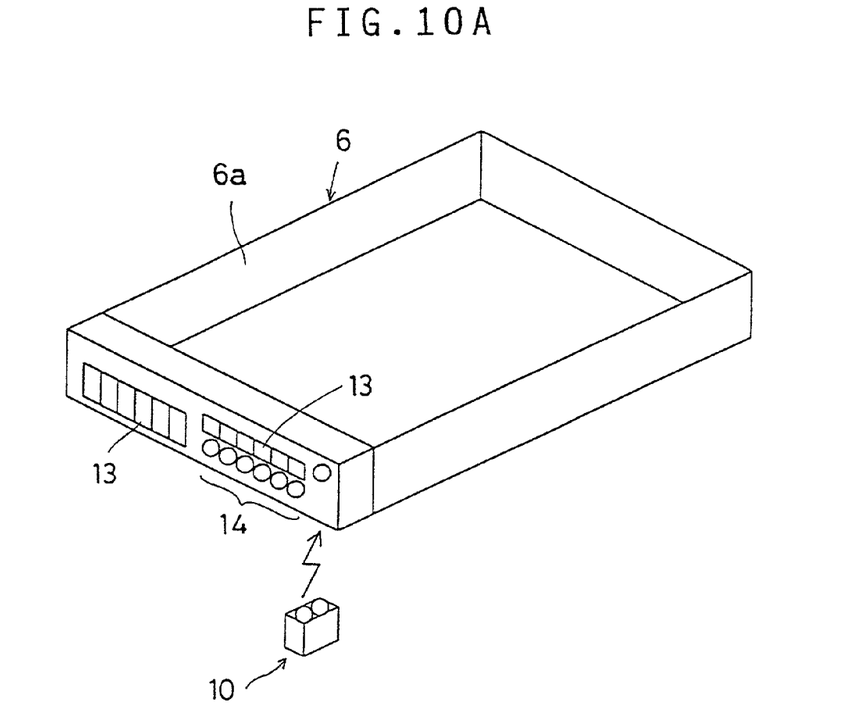
FIG. 10A is a perspective view of a tray.

Each tray 6 has its own microcomputer including a CPU (central processing unit) 12 which receives prescription data through an infrared transmission unit 11, and displays the data on a liquid crystal display 13. When the CPU 12 receives a switch signal from a button switch 14, it returns necessary signals to the CPU 3a of the control unit 3 through the infrared transmission unit 11. FIG. 10A shows the appearance of the tray 6. Its use and operation will be described later.

In the above arrangement, the CPU with a memory, CRT display, keyboard, mouse and file device, are all dedicated to a personal computer. Alternatively, the file device may be arranged as an independent server, connected to the CPU through a network in a server-client (CPU) relation.

In the printer setting portion 3b1, setting data are stored which specify which printers (indicated in numbers) correspond to which drug types (indicated in codes) to set which printers are to be used to print data on the respective drug types. The data memory 3b2 stores basic data including all the drug codes for determining the drug name, unit and drug type code for each drug code in the form of a list.

Figure 3:
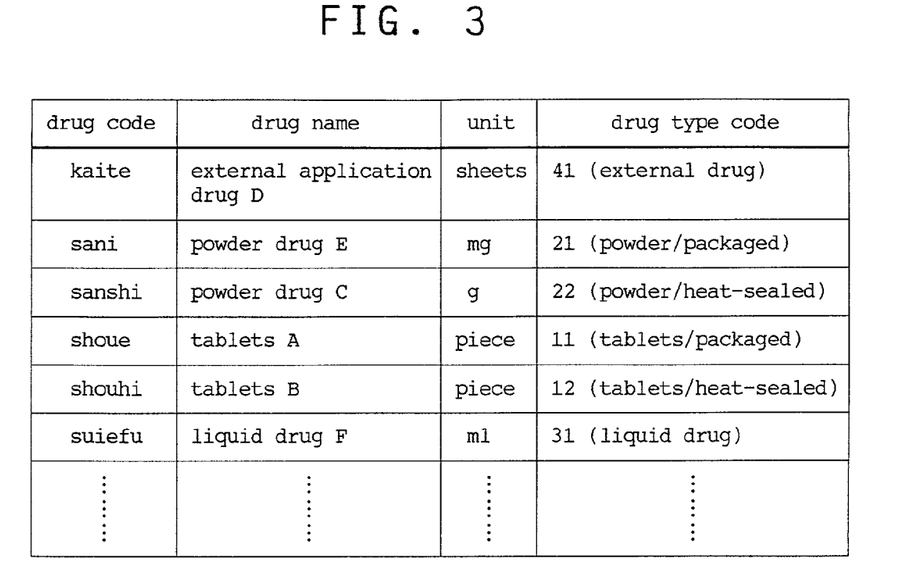
FIG. 3 is a list showing relation between drug codes and drug type codes registered in the data storage portion.

The basic data stored in the data memory 3b2 are stored in files generally called master files. These files include a drug master file, patient master file, master file concerning how to take drugs, and other auxiliary files including department master files and doctor master files. A specific example of drug master file is shown in FIG. 3.

As shown, a drug master file lists drug codes, drug names, units and drug type codes in a list form. Drug codes are shown in the form of abbreviations of Japanese characters. Drug type codes are as explained in the "Prior Art" section. That is, ID numbers such as 11, 12, 21, 22, 31, 41 are affixed to "tablets, packaged", "heat-sealed tablets", "powder drugs, packaged", "heat-sealed powder drugs", "liquid drugs", "externally applied drugs", respectively.

Figure 4:
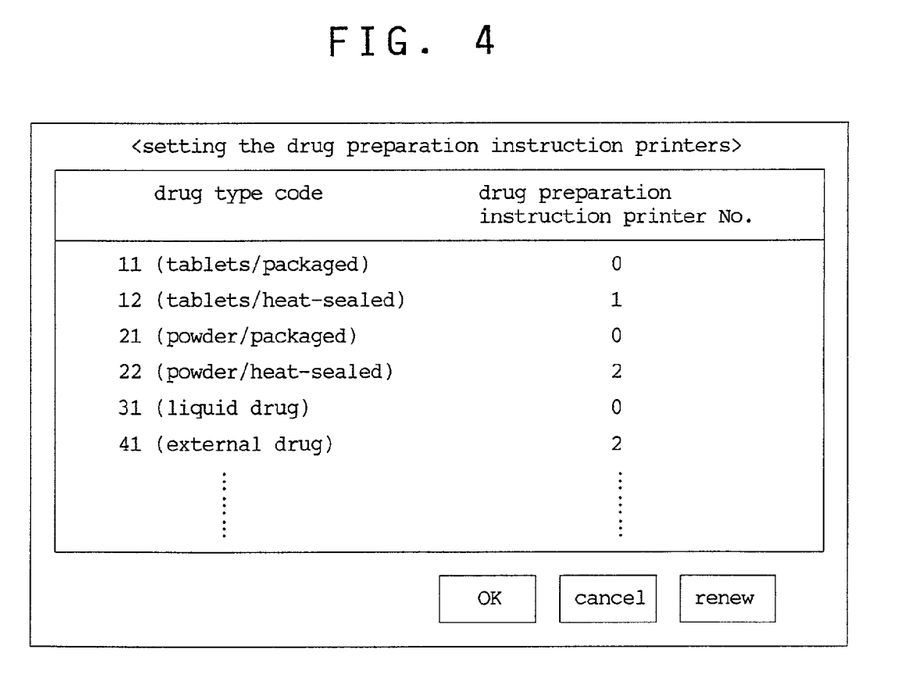
FIG. 4 is a chart showing data set in the printer setting portion.

The printer setting function by the printer setting memory 3b1 is explained below. When a drug code signal of drug data inputted for a particular patient coincides with any of various drug type codes stored in the drug master file shown in FIG. 3, so that drug type codes prescribed for this patient are read, setting data in which the numbers of printers are affixed to the respective drug type codes are read out from the printer setting memory 3b1. Thus, printers whose numbers correspond to the designated drug type codes are read as shown in FIG. 4. As a result, a control signal for printing items necessary for preparing drugs corresponding to the designated drug type codes is given. Printers of the designated numbers are printed. Numbers in the figure indicate printer numbers. Number 0 has no designation, that is, it indicates that printing is not to be made.

In the printer setting data, the printer numbers designated for various drug type codes are recorded beforehand as a printer setting file. When it is necessary to change the correlation of the printer numbers due e.g. to relocations in the pharmacy, this can be done simply by changing printer numbers of the setting data in this file.

If it is desired to change the printer number setting, the printer setting screen (FIG. 4) is activated to display what is recorded in the file, and the mouse is clicked at a position to be changed to move the input cursor to this position, and write the new printer number on this position through keyboard. Then by clicking the "OK" button with the mouse, file renewal (writing) ends with the information on the screen recorded. If the cancel button is clicked, the screen ends without renewing the file. If the "renewal" button is clicked, the screen does not end with only the file renewed.

Figure 5:
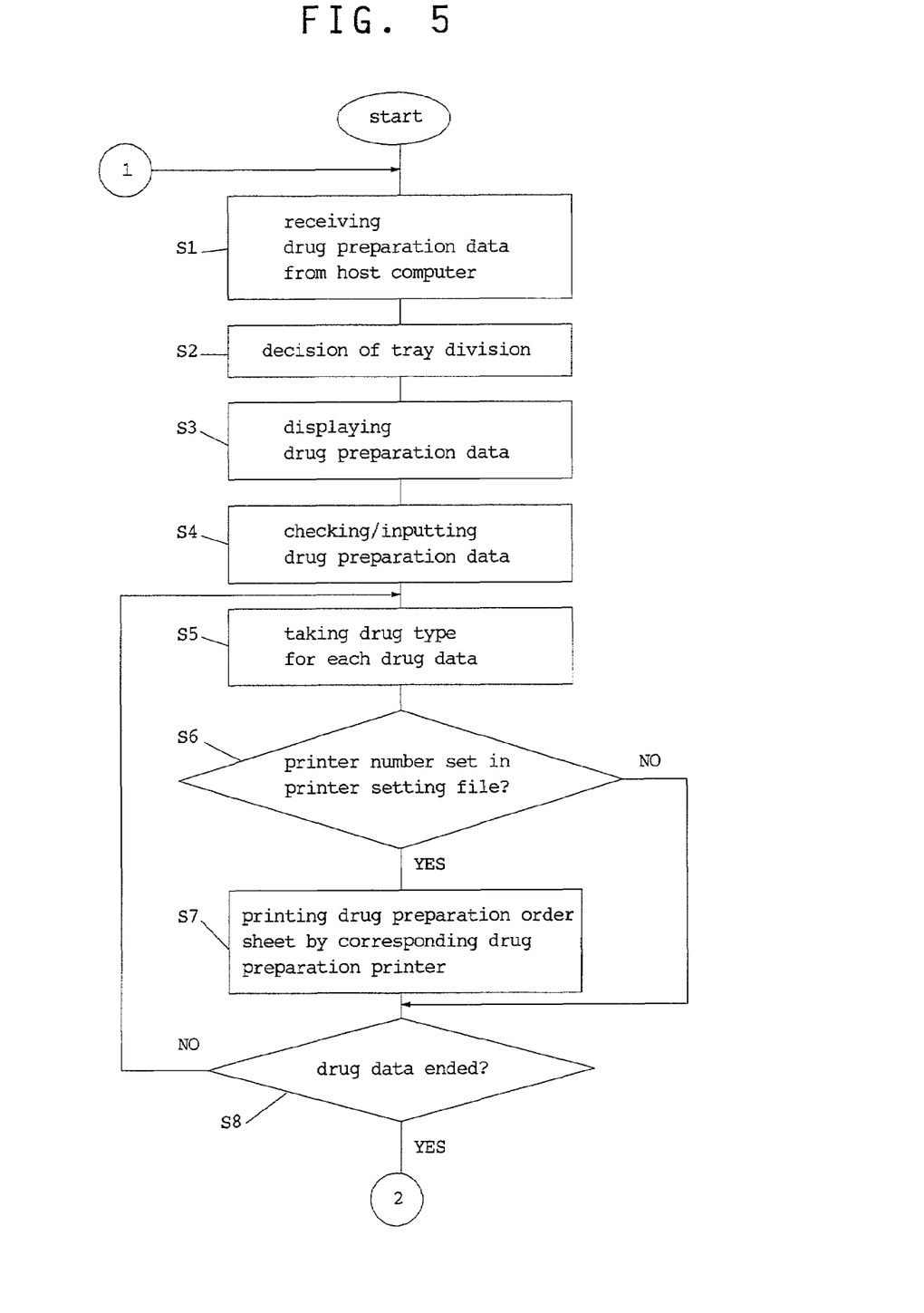
FIG. 5 is a flowchart showing the drug preparation order flow.
Figure 6:
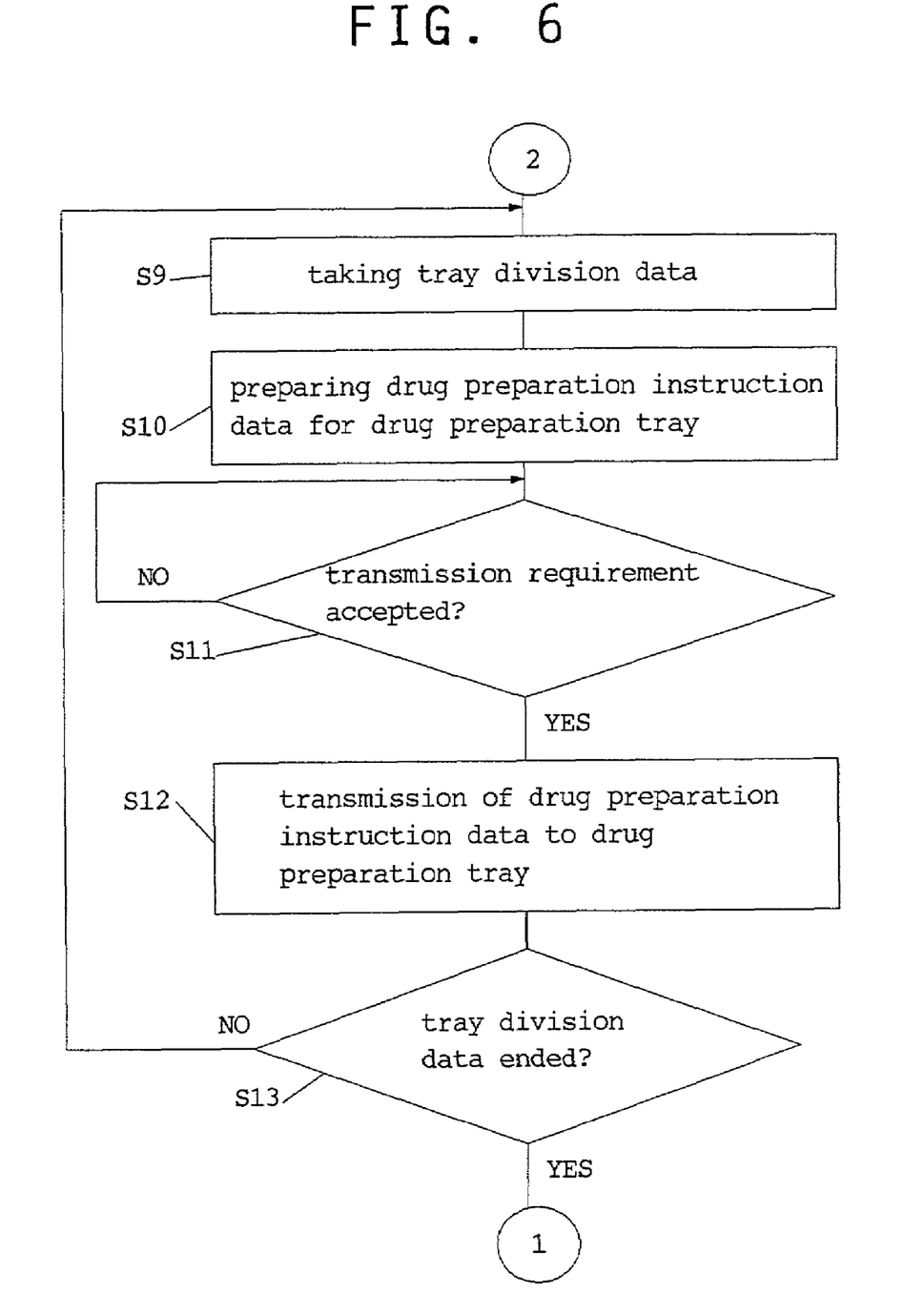
FIG. 6 is another flowchart of the drug preparation order flow.

In the system of this embodiment, drug preparation instructions are given by the printers as shown in the flowchart of FIGS. 5 and 6 as follows. In Step S1, drug preparation data transmitted from the host computer 9 are received. When the data are received, they are usually inputted from the host computer in a code form that is convenient for the host computer. Such a code form may however not be suitable for the system of the present invention. In such a case, the data are changed to a code form convenient for the present system. But if drug preparation data are inputted through the input means such as keyboard 7 and/or mouse 8, drug preparation data are received in a code form suitable for the present system in Step S1.

In S2, tray division is determined. The drug data for each patient includes drug types, dosage for each time, and the number of days for which the drugs have been prescribed. In S2, the number of trays used is determined based on this data. If the number of days is greater than a predetermined value, a plurality of trays are used for one patient.

But if too many trays are used for each patient, handling becomes difficult, the cost increases, and a larger space is needed. Thus, the number of trays used for each patient should be determined taking into consideration past experiences.

Generally speaking, if drugs are prescribed for a large number of days, the amount of the drugs is correspondingly large. Among the drug types, "heat-sealed tablets" (ten tablets are usually packaged in each bag) are liable to drop off trays. Thus, these types of drugs should be put in extra trays that are separate from other types of drugs. It is to be understood that the term "tablets" herein used include capsules, and the term "heat-sealed" encompasses PTP (Press Through Package) packaging.

For how many days drugs should be given varies from one pharmacy to another and should be adjusted within the range of from 30 to 90 days. In some pharmacies, "heat-sealed tablets" may be put in one tray, "externally applied drugs" and "liquid drugs" in another, and all the others in still another tray.

In Step S3, the drug prescription data are displayed on the CRT display 5 for confirmation. Since only drug code data are used for drugs, and only code data are used for patients, taking directions, departments and MD's, corresponding drug names, patient names, taking directions, departments and MD's names are read from the respective files and drug preparation data are displayed in such a format as shown in FIG. 7.

In Step S4, a pharmacist visually checks the drug preparation data thus displayed, to see if there is anything wrong in the data. In this step, the pharmacist ensures that the respective data are proper based on prescriptions prepared by doctors. If any flaw is found in the data, the displayed data portion is clicked for correction. When an "inspection OK" button provided at the bottom of the screen is clicked, the process proceeds to the next step.

Figure 7:
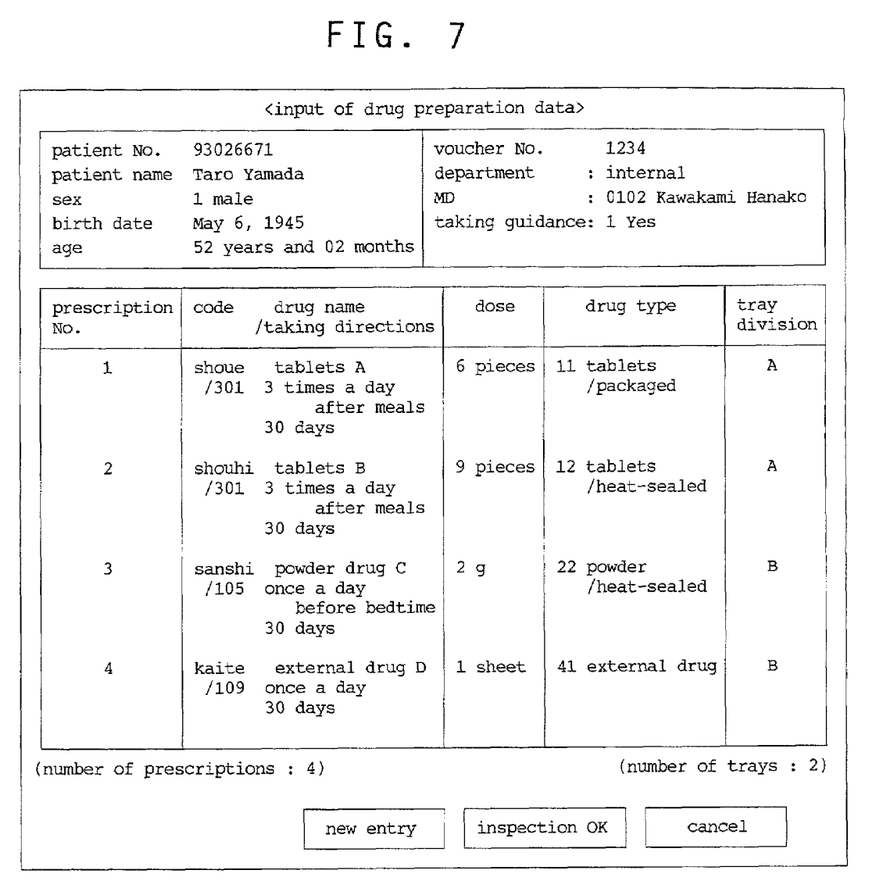
FIG. 7 is an example of drug preparation data.

As shown in FIG. 7, when the drug preparation data are shown, the screen display includes division into trays and whether or not taking guidance is necessary. A, B in the tray division column indicate that drugs should be put in two trays 6a and 6b of the trays 6. If no division into trays is necessary, this part of the screen remains blank. Numerals 1 and 2 in the taking guidance section of the screen indicate that taking guidance is necessary and not necessary, respectively. How drug preparation data are transmitted to trays is described later.

The number of prescription indicated under the prescription number column indicates the total number of prescription. The tray number under the tray division column indicates the total number of trays used. If tray division is done forcibly to a given number, the divided portion is clicked with the mouse to move the input cursor, and ID symbols such as "A" and "B" are changed by overwriting through the keyboard. When the "cancel" button is clicked, the drug preparation data displayed at that time are stored and erased from the screen for later processing so that a pharmacist can enter new drug preparation data for another patient number.

When the drug preparation data have been determined, printer setting is checked in the later steps. First in S5, drug types for the respective drug data are taken. Then in S6, it is determined whether or not printer numbers are set for the respective printer in setting files. This determination is carried out automatically for each drug data in the control unit 3. If printer numbers are set for the respective drug data necessary for a patient (YES), a drug preparation order sheet is printed by the printer of the corresponding number in Step S7.

Figure 8:
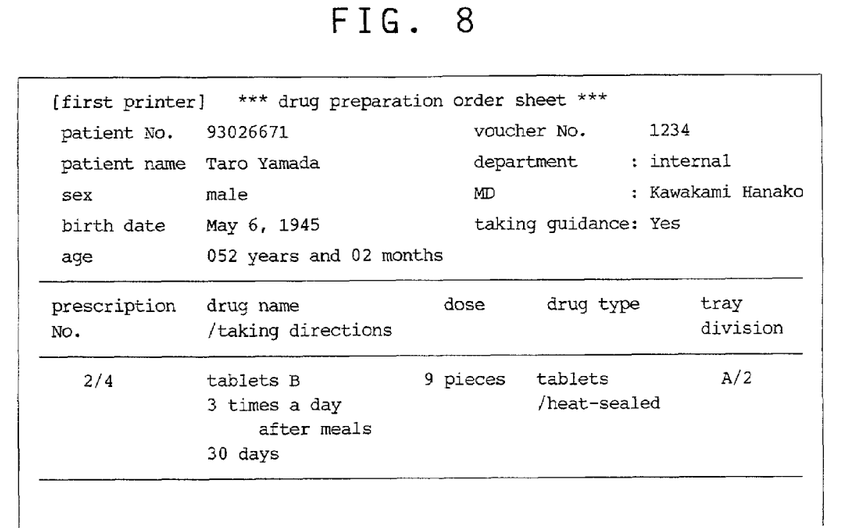
FIG. 8 shows information printed by a first printer.
Figure 9:
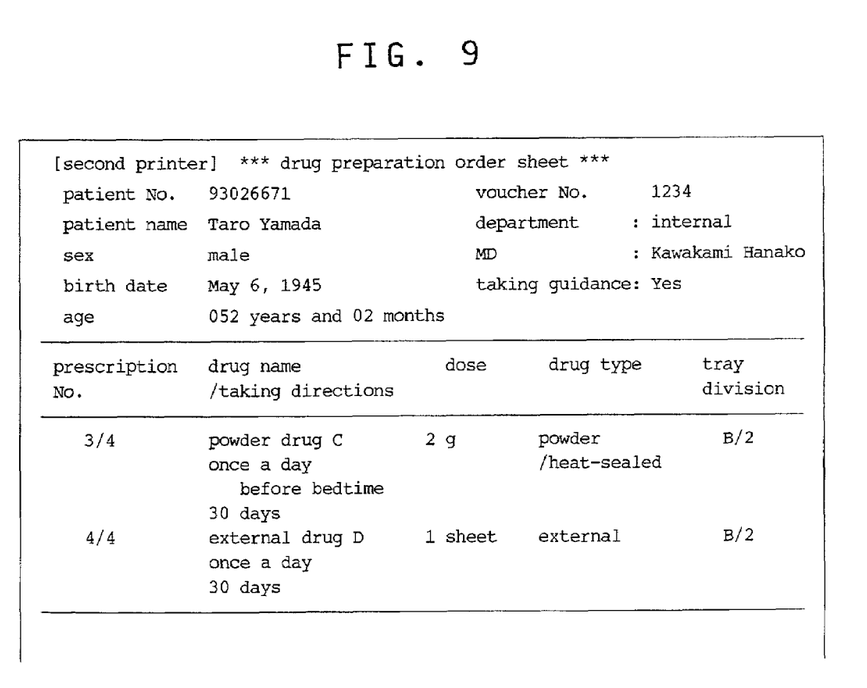
FIG. 9 shows data printed by a second printer.

An example of a drug preparation order sheet is shown in FIGS. 8 and 9. FIG. 8 indicates that among the prescription numbers of drug preparation data shown in FIG. 7, No. 2 has been printed on a drug preparation order sheet by the first printer. FIG. 9 indicates that Nos. 3 and 4 have been printed on drug preparation order sheets by the second printer. Since tablets A in prescription No. 1 are packaged by an automatic packaging machine, no drug preparation orders are indicated by any printer. Each of the above drug preparation order sheets contains tray division such as (A/2), (B/2), and whether or not taking guidance is necessary. In the illustrated example, one kind of drug corresponds to one prescription number. But each prescription number may include a plurality of drugs. The print is carried out for each drug.

When the drug preparation order sheets have been printed, checking is made in S8 on whether or not printing has ended. If not ended, unprocessed drug data are processed in S5. If no printer number is set for the drug data in Step S6 (NO), the program also proceeds to S8 to check if drug data have been processed.

When the checking in Step S8 has ended, tray division data are taken in S9. This is to take ID symbols (A or B) from the tray division indication in the shown in FIG. 7. This is because these ID symbols indicate trays 6a, 6b. In S10, based on these ID symbols, drug preparation order data are prepared for trays.

Figure 10B:
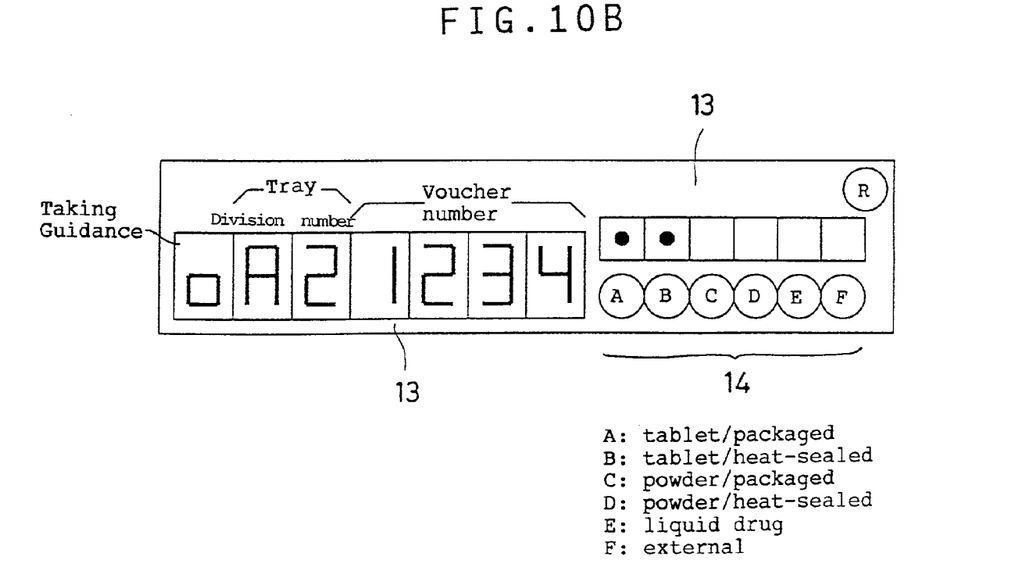
FIG. 10B is a view showing the display on the tray.

Preparation of drug preparation order data is necessary because if drugs are put in two or more trays, drug data to be put in the respective trays have to be transmitted and displayed. FIG. 10A shows an entire view of a tray and FIG. 10B is a partial enlarged view of its display.

The display portion of the tray displays on its liquid display portion 13 whether or not taking guidance is necessary, the number of trays to be used, voucher number, drug type, etc. Various drug type instructions are displayed on button switches 14. The symbols ● in the liquid crystal display over the button switches 14 indicate drug types to be put in the tray. In the illustrated example, tablets to be packaged and heat-sealed tablets are to be put in the tray. When the intended drugs are put in the tray, a pharmacist presses the buttons under ● to turn them off so that anyone can see that necessary drugs have been put in the tray.

When the drug preparation instruction data have been prepared for the drugs to be put in the respective trays 6a, 6b, transmission instruction are sent to the trays 6a, 6b from the infrared transmission unit 10 shown in FIG. 2 in S11. It is checked whether or not the transmission instructions have been received by the trays 6a, 6b. When the transmission instructions have been entered, drug preparation data are sent to the tray that has received the transmission requirements, e.g. tray 6a.

By this transmission, minimum necessary information that has to be displayed on the tray such as whether or not taking guidance is necessary, the number of trays to be used, voucher number, etc. is displayed on the display 13 of the tray as mentioned earlier. When the transmission ends for the tray 6a, whether or not tray division data to be transmitted for another tray 6b have been transmitted is checked in Step S13. Since data have not yet been transmitted for tray 6b, the program returns to a step before S9 and carries out the same operation for tray 6b.

When drug preparation instruction operations for one patient ends, the program returns to the beginning of Step S1 and repeats drug preparation operations for the next patient.

According to the drug preparation instruction system of the above embodiment, printers are designated for the respective drug types by reading designated printers from the printer setting file, and drug preparation instructions are given based on drug preparation order sheets printed by printers. If it is necessary to change the correlation between the printers and the drug types due e.g. to relocations in the pharmacy, any layman can do this simply by changing the printer number setting data without the help of a professional system programmer.

In order to put drugs in a plurality of trays, information for displaying the contents of the drug types to be put in each tray is transmitted from the drug preparation instruction system, so that if the amount of drugs for one patient is large, they are put in a plurality of trays, and the drug types are displayed on each tray. Thus, drugs can be put accurately in each tray. Since drugs are put in a plurality of trays, there is no need to hand-carry drugs that cannot be put in a single tray. This saves trouble.

Since whether or not taking guidance is necessary is displayed on each tray, a pharmacist can check this instantly without the need to read the drug preparation order sheet, so that a pharmacist at the drug delivery counter can instantly check his or her workload.

As described above, according to the drug preparation order system of this invention, information printed by each of a plurality of printers, such as drug names, taking directions, dosage, drug types, is instructed and controlled from the control device. Printer setting data corresponding to the respective drug type codes are read from the printer setting portion and printed by printers corresponding to the drug contents. Printers can thus be easily set by making setting data for the printers. Even if it is necessary to change the correlation between the drug type codes and the printers due e.g. to relocations in the pharmacy, this can be done easily by simply changing the data for setting the drug type-to-printer relations. Workability thus improves.

What is claimed is:

1. A drug preparation order system for use with a drug preparation order sheet, said system comprising:
   a control unit for carrying out logic operations and outputting control signals;
   a display device connected to said control unit; and
   a plurality of printers connected to said control unit,
   said control unit comprising:
   a memory for storing a plurality of printer codes each corresponding to one of said plurality of printers, a plurality of drug type codes, and a printer setting file defining a correlation between the drug type codes and the printer codes;
   an input device through which external data can be entered into said memory, said external data comprising a plurality of sets of data, each set comprising drug data;
   correlating means for correlating each of the plurality of sets of data with one of the drug type codes;
   display means for displaying said correlation between the drug type codes and the printer codes on said display device;
   altering means for altering said correlation between the drug type codes and the printer codes in response to a signal entered through said input device; and
   printer activating means for, in response to a command to print one of the plurality of sets of data, activating one of said printers that corresponds to one of the printer codes corresponding, in accordance with said printer setting file, to one of said drug type codes which is correlated by said correlating means with said one of the plurality of sets of data to print said one of the plurality of sets of data on a drug preparation sheet.

2. The system of claim 1, further comprising:
   a first type of communicator connected to said control unit, said first type of communicator being operable to transmit drug preparation order data provided by said control unit,
   a plurality of trays, each having a second type of communicator, said plurality of trays and said control unit being combined as a system,
   wherein each of said second type of communicators is operable to communicate with said first type of communicator,
   wherein each of said trays has a display portion, and
   wherein said display portions are operable to display the drug data.

3. The system of claim 2, wherein said printers are operable to print on a drug preparation order sheet, information indicating whether drugs have been put into one of said plurality of trays,
   wherein said control unit is operable to transmit identification information to said trays when drug data is transmitted by said first type of communicator, and
   wherein said control unit is operable to transmit information on whether guidance is necessary when drug data is transmitted by said first type of communicator.

4. The system of claim 2, wherein said control unit is operable to transmit identification information to said trays when drug data is transmitted by said first type of communicator, and
   wherein said control unit is operable to transmit information on whether guidance is necessary when drug data is transmitted by said first type of communicator.

5. The system of claim 2, wherein said control unit is operable to transmit information on whether guidance is necessary when drug data is transmitted by said first type of communicator.

6. The system of claim 2, wherein in order to put drugs into said plurality of trays according to drug types and a number of days for which the drugs are to be prescribed, the drugs can be assigned to said plurality of trays,
   wherein said printers are operable to print on a drug preparation order sheet, information indicating whether drugs have been put into a plurality of trays, wherein said control unit is operable to transmit identification information to said trays, when drug data is transmitted by said first type of communicator, and
   wherein said control unit is operable to transmit information on whether guidance is necessary, when drug data is transmitted by said first type of communicator.

* * * * *